United States Patent
Hayward et al.

(10) Patent No.: US 7,333,919 B2
(45) Date of Patent: Feb. 19, 2008

(54) PERTURBATION DETECTION

(75) Inventors: Stephen David Hayward, Malvern (GB); Timothy Ingram Cox, Malvern (GB); Marie Harper Anderson, Malvern (GB)

(73) Assignee: Qinetiq Limited (GB)

( * ) Notice: Subject to any disclaimer, the term of this patent is extended or adjusted under 35 U.S.C. 154(b) by 562 days.

(21) Appl. No.: 10/508,480

(22) PCT Filed: Mar. 19, 2003

(86) PCT No.: PCT/GB03/01166

§ 371 (c)(1),
(2), (4) Date: Sep. 21, 2004

(87) PCT Pub. No.: WO03/083457

PCT Pub. Date: Oct. 9, 2003

(65) Prior Publication Data

US 2005/0156101 A1   Jul. 21, 2005

(30) Foreign Application Priority Data

Mar. 28, 2002   (GB) ................................. 0207431.8

(51) Int. Cl.
*G06F 11/30* (2006.01)
*G06F 15/00* (2006.01)

(52) U.S. Cl. .................................... 702/185; 702/183

(58) Field of Classification Search ............... 702/182, 702/185, 189, 76, 77, 34, 35, 183; 250/227.14, 250/226, 339.09
See application file for complete search history.

(56) References Cited

U.S. PATENT DOCUMENTS

| 4,796,994 A | | 1/1989 | Bager |
| 5,057,992 A | * | 10/1991 | Traiger ........................ 700/52 |
| 5,179,525 A | | 1/1993 | Griffis et al. |
| 5,963,658 A | * | 10/1999 | Klibanov et al. ........... 382/128 |
| 6,202,033 B1 | | 3/2001 | Lange |
| 6,448,758 B1 | * | 9/2002 | Krahn et al. ............. 324/158.1 |
| 6,518,573 B1 | * | 2/2003 | Hoult .................... 250/339.09 |
| 2001/0044119 A1 | | 11/2001 | Ghadiri et al. |

FOREIGN PATENT DOCUMENTS

| EP | 0 299 403 | 1/1989 |
| WO | WO 99/12305 | 3/1999 |
| WO | WO 99/31527 | 6/1999 |
| WO | WO 00/26665 | 5/2000 |
| WO | WO 00/74331 | 12/2000 |
| WO | WO 01/23968 | 4/2001 |

* cited by examiner

*Primary Examiner*—Bryan Bui
(74) *Attorney, Agent, or Firm*—McDonnell Boehnen Hulbert & Berghoff LLP

(57) ABSTRACT

A method for detecting perturbation of a physical system from a reference state associated with a reference parameter ($\omega_0$) to a perturbed state associated with a perturbed parameter ($\omega$) includes firstly deriving the reference parameter ($\omega_0$). A reference vector (F) is then derived which describes the system's state at the reference parameter ($\omega_0$). A measurement-related vector (Z) associated with a perturbed state of the system is then subtracted from the reference vector (F) to provide an error vector (E). The error vector members are summed and normalised by division of a summation of elements of a vector (F') representing a derivative ($f(\omega_0 \delta \omega)_e$) of a reference itself represented by the reference vector (F), the derivative ($f(\omega_0 \delta \omega)_e$) being evaluated at the reference parameter ($\omega_0$). This provides a result equal to the difference ($\omega - \omega_0$) between the perturbed parameter ($\omega$) and the reference parameter ($\omega_0$).

42 Claims, 8 Drawing Sheets

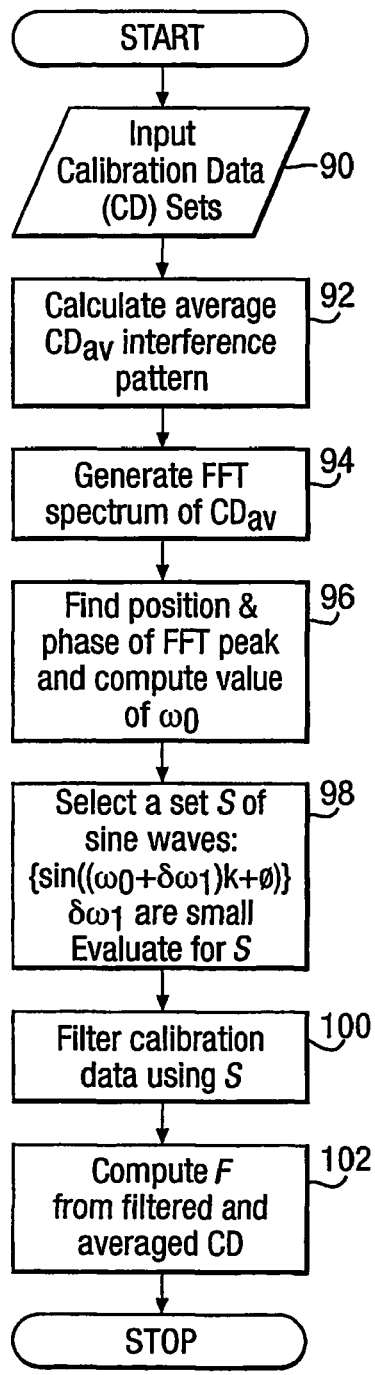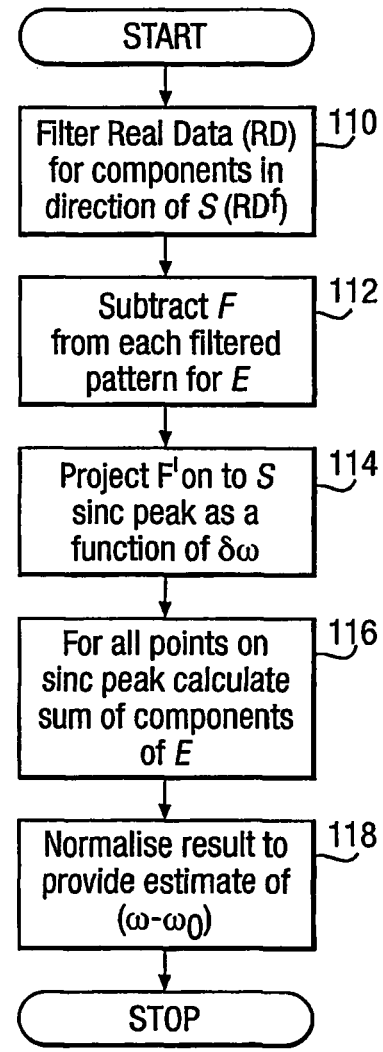

PERTURBATION DETECTION

BACKGROUND OF THE INVENTION (1) Field of the Invention

This invention relates to detecting perturbation, and more particularly to a method, an apparatus and a computer programme for detecting perturbation of a physical system's state from a reference state. A useful application of this invention is to detection of perturbation of the state of a sensitive detection system such as a porous silicon biosensor by an optical technique.

(2) Description of the Art

Porous silicon is known to be suitable for fabrication into sensitive detectors. The nature of porous silicon allows a ready response at a microscopic level to perturbations caused by environmental changes. Moreover, porous silicon lends itself to interferometric techniques: well-resolved Fabry-Perot fringes may be generated on illumination of a layer of the material providing a basis for sensitive interferometric detection of its microscopic response. The response may simply be absorption or trapping of molecules in the pores of the silicon or it may be made more specific by grafting a recognition agent to an internal surface of the pores. In either case, any molecular event occurring within a porous silicon layer will affect the layer's optical properties, resulting in a change in an interference fringe pattern which can be detected and quantified if of sufficient magnitude.

Sailor et al. in WO99/12305 describe a porous silicon-based biosensor. Biosensors in general consist of two components: a recognition agent which reacts to produce a molecular or chemical signal in the presence of a specific reagent and a signal transducer which converts the molecular recognition event into a quantifiable signal. The recognition agent used in a porous silicon biosensor may be, for example, an antibody grafted into the layer and so a molecular reaction will occur in the presence of a specific antigen. Occurrence of such a reaction is observed via an optical interference pattern.

In any periodic interference pattern, such as produced by the biosensor described in WO99/12305, the separation between peaks is proportional to the optical path difference between alternative routes taken to a detector as the incident beam is partially reflected at interfaces. Under such circumstances, an accepted analysis technique is to locate peaks in the Fourier transform spectrum of the interference pattern. The location of such peak(s) provides an indication of fringe spacing(s) in the original pattern, from which a value for optical path difference can be derived. As will be described in more detail later, the interference pattern developed using a porous silicon biosensor is collected as a discrete set of spectral data points. One of the standard fast Fourier transform (FFT) algorithms is therefore used as the basis for Fourier analysis. The details of such an approach to analysing signals from a porous silicon biosensor are described by Janshoff A. et al. in J. Am. Chem. Soc. 120 pp 12 108-12 116 (1998). There are however various drawbacks to using this method of analysis, particularly in situations such as provided by the porous silicon biosensor in which the monitored binding event is capable of highly sensitive discrimination. Although the Fourier transform method per se (i.e. finding the position of the peak in amplitude of the Fourier transform of the data) is known to be optimal in locating the frequency of a single tone in white noise, many actually measured signals do not sufficiently approach this ideal and so do not allow full exploitation of the method's capabilities. Moreover, use of the FFT in particular involves interpolation in the transform spectrum between regular sampling points. This severely limits the accuracy with which a peak in the transform can be located.

There is generally a need for increased sensitivity in any detection system, and this can be achieved either by rendering a detecting medium more responsive to events to be detected or by improving extraction of required data from an inevitably-noisy experimentally detected signal. More sensitive biosensors will aid, for example, early detection of a disease antigen or rapid detection of the presence of explosives. It is an object of the present invention to provide an alternative form of perturbation detection.

SUMMARY OF THE INVENTION

The present invention provides a method of detecting perturbation of a physical system from a reference state associated with a reference parameter to a perturbed state associated with a perturbed parameter ($\omega$), characterised in that the method includes the steps of:

a) deriving the reference parameter;

b) deriving a reference entity which describes the system's state at the reference parameter;

c) deriving an error entity from the difference between the reference entity and a measurement-related entity associated with a perturbed state of the system; and d) using the error entity to provide an indication of whether or not the system state has been perturbed from the state associated with the reference parameter, with the perturbed parameter having become unequal to the reference parameter.

The expression 'entity' is used to mean a vector member, a vector or a function.

The invention provides for detection of perturbation with respect to a reference parameter and responds to a change from this indicated by the perturbation parameter. Such change is normally small, and so the invention provides the advantage that it makes it possible to employ mathematical approximations which are applicable to small changes in parameters.

The error entity may be a vector with multiple members and step d) then includes calculating the sum of the error vector's members to obtain an indication of whether or not the perturbed parameter has become unequal to the reference parameter. The error entity may have members characterised by relatively high signal to noise ratio compared other possible members which might otherwise be selected for deriving it. It may have members derived from a region of a peak in a derivative of the reference entity.

Prior to derivation of the error entity in step c), the measurement-related entity is normalised by projection on to a space orthogonal to that of the reference entity. Step d) may include determining the difference between the perturbed and reference parameters by error entity normalisation with respect to an entity which is the summation of elements of an entity representing a derivative of a reference function evaluated at the reference parameter, the reference function being represented by the reference entity.

Step b) may incorporate:

a) predicting from the reference parameter a position of a peak in a Fourier transform spectrum of observation data;

b) selecting a subset of the observation data over the predicted peak calculating a direct Fourier transform (as herein defined) for the subset; and c) analysing the direct Fourier transform in order to derive a more accurate determination of the position of the peak.

The reference entity may be derived in step b) by a process which includes filtering by projection of an entity on to a set of pre-determined entities having a range of arguments all of which differ from the reference parameter by less than one tenth of the reference parameter.

Step c) of the method may comprise calculating the error entity by a process including deriving the measurement-related entity by a process which includes data filtering by projection of a measurement entity on to the set of pre-determined entities.

The reference entity may be derived in step b) from an average of a series of observation data vectors. These vectors may be time-varying and this may be taken into account when their average is derived. The reference entity may be a sum of a static reference entity and a linearly time-varying entity.

The physical system may be a sensor pervaded by a medium having variable composition. The sensor may be a porous silicon sensor with pores pervaded by a solvent medium, the perturbed and reference parameters are then optical thicknesses of a region of the sensor pervaded by different solvent compositions and in which interference patterns are generated for derivation of the reference entity and error entity.

In an alternative aspect, the present invention provides apparatus for detecting perturbation of a physical system from a reference state associated with a reference parameter to a perturbed state associated with a perturbed parameter, characterised in that the apparatus includes:

a) a monitoring device for monitoring the physical system to obtain indications of the system's state;
b) a computer system programmed to process the system state indications to:
  i) derive the reference parameter ($\omega_0$);
  ii) derive a reference entity (F) which describes the system's state at the reference parameter ($\omega_0$);
  iii) derive an error entity (E) from the difference between the reference entity (F) and a measurement-related entity (Z) associated with a perturbed state of the system; and
  iv) use the error entity (E) to provide an indication of whether or not the system state has been perturbed from the state associated with the reference parameter ($\omega_0$), with the perturbed parameter ($\omega$) having become unequal to the reference parameter ($\omega_0$).

In a further alternative aspect, the present invention provides computer software for use in detecting perturbation of a physical system from a reference state associated with a reference parameter to a perturbed state associated with a perturbed parameter, characterised in that the software contains instructions for controlling a computer to implement the steps of:

a) deriving the reference parameter;
b) deriving a reference entity which describes the system's state at the reference parameter;
c) deriving an error entity from the difference between the reference entity and a measurement-related entity associated with a perturbed state of the system; and
d) using the error entity to provide an indication of whether or not the system state has been perturbed from the state associated with the reference parameter, with the perturbed parameter having become unequal to the reference parameter.

The apparatus and software aspects of the invention may have preferred features equivalent mutatis mutandis to those of the method aspect.

DESCRIPTION OF THE FIGURES

Embodiments of the invention will now be described, by way of example only, with reference to the accompanying drawings, in which:

FIG. 6 is a flow chart of steps involved in deriving a filtered calibration function for use in the present invention;

FIG. 9 is a flow chart of the steps involved in analysing data in accordance with the analysis system of the present invention;

DESCRIPTION OF A PREFERRED EMBODIMENT

Figure 1:
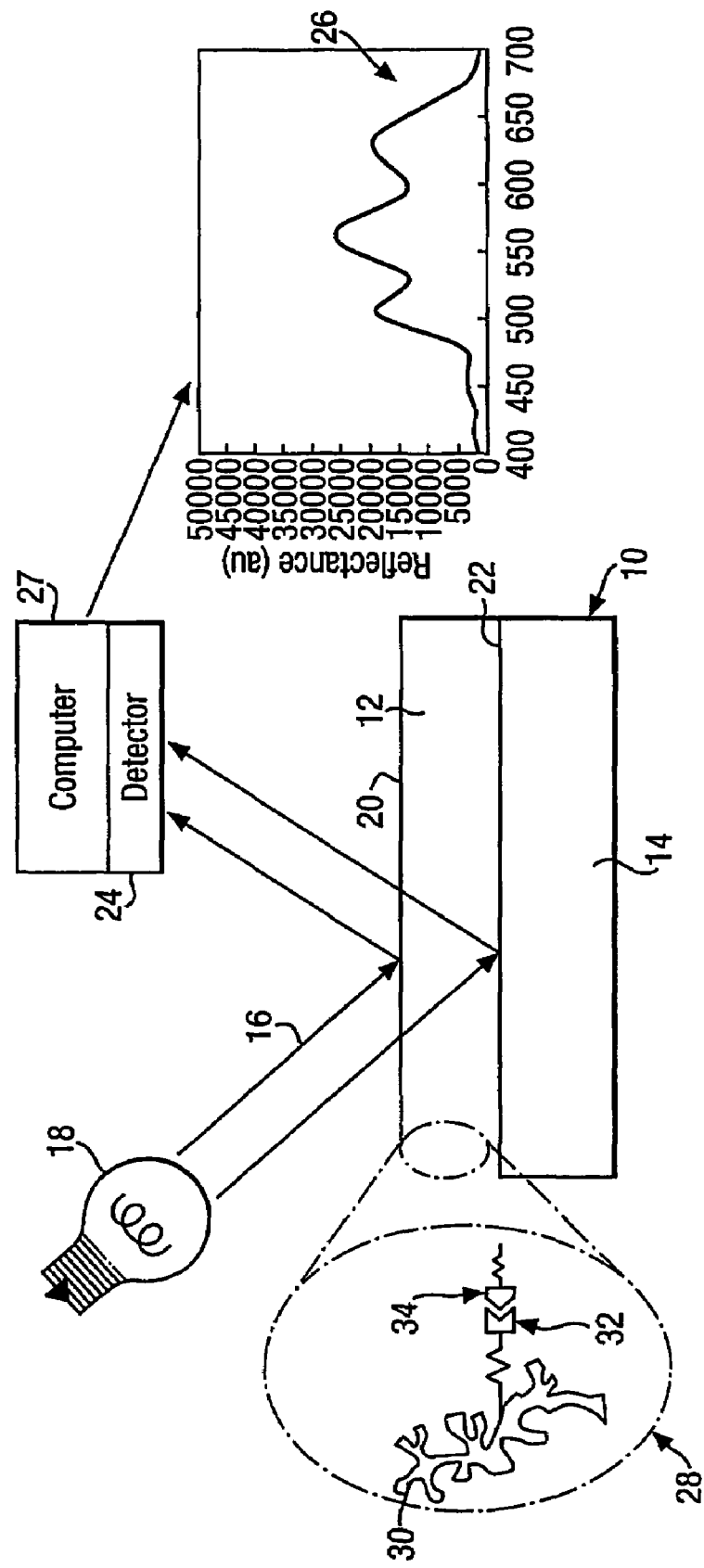
FIG. 1 is a schematic illustration of a porous silicon biosensor for use in perturbation detection in accordance with the invention.

Referring to FIG. 1 a porous silicon biosensor 10 can be used to provide experimental results which are particularly suited for perturbation detection by embodiments of the present invention. Basic principles of use of the biosensor 10 are as follows. The biosensor 10 comprises a porous silicon layer 12 on a bulk (substantially non-porous) silicon substrate 14. When the porous layer 12 is illuminated by light 16 from a white light source 18, the light 16 is reflected at interfaces 20, 22 between the porous silicon layer 12 and air and between the porous silicon layer 12 and the bulk substrate 14. Reflected light is detected by a CCD detector 24. Reflection at the two interfaces 20, 22 gives rise to two reflected beams which interact with each other to generate an interference pattern 26, which is detected at the detector 24. Signals detected by the detector 24 are processed by a computer system 27.

The interference pattern 26 is essentially a measurement of the intensity of light reflected from the biosensor 10 as the light wavelength is varied across the white light spectrum. In practice, alternative measures of intensity such as reflectance (in the pattern 26 shown in FIG. 1) or voltage developed at the detector 24 (see FIG. 2) are used to provide an indication of the amplitude of the interference pattern 26. Whatever measure is used however, interference peaks will occur at wavelengths $\lambda_{max}$ when the well-known interference condition is satisfied:

$$2n(\lambda_{max})d = m\lambda_{max} \qquad (1)$$

where d is the thickness of the porous silicon layer 12, $n(\lambda_{max})$ is the refractive index of the layer 12 at wavelength $\lambda_{max}$, is an integer and normal incidence of the light 16 on the layer 12 is assumed.

A magnified view 28 of a region of the porous silicon layer 12 is also shown in FIG. 1. This view 28 depicts in microstructure a representation of the porous silicon material 30 on to which is grafted a recognition agent 32. In this instance, the recognition agent 32 is illustrated bound to an analyte 34, for which it is a specific identifier. The recognition agent 32 might, for example, be an antibody for a chemical agent or for an explosive.

In the absence of the analyte 34, the porous silicon 12 with grafted recognition agent 32 exhibits particular optical properties, and these properties enable an interference pattern to be generated with peaks in accordance with Equation (1). If the analyte 34 is present in the environment however, then some proportion will bind to the recognition agents 32 within the porous layer 12 which in turn will affect the optical properties of that layer. Specifically, layer thickness will remain unchanged, but the refractive index $n(\lambda_{max})$ of the layer will be affected by the additional bonded molecule. This will be evidenced as a movement in the positions of the interference peaks, as dictated by Equation (1).

It is to be noted that, strictly, the refractive index n of the layer is wavelength dependent, hence use of the $n(\lambda_{max})$ notation. In a practical application of the method described here, it is assumed that the layer refractive index is independent of wavelength and use is made of an average value over the range of illuminating wavelengths employed. Accordingly, the layer refractive index referred to in Equation (1) will be denoted $n_{avg}$ when descriptions of practical implementations are given.

It is readily apparent from Equation (1) that the spacing between adjacent maxima in the interference pattern provides an indication of $n_{avg}d$. If the interference spectrum in the absence of the analyte is known, then observation of the interference spectrum 26 developed from a biosensor 10 in an unknown environment will provide an indication as to whether the analyte 34 is present or absent in that environment. As interferometry may be extremely sensitive, it is to be expected that, in principle, even small amounts of bound analyte can be detected using this biosensor. Firstly however, some means of analysing and interpreting the interference spectrum must be developed.

Figure 2:
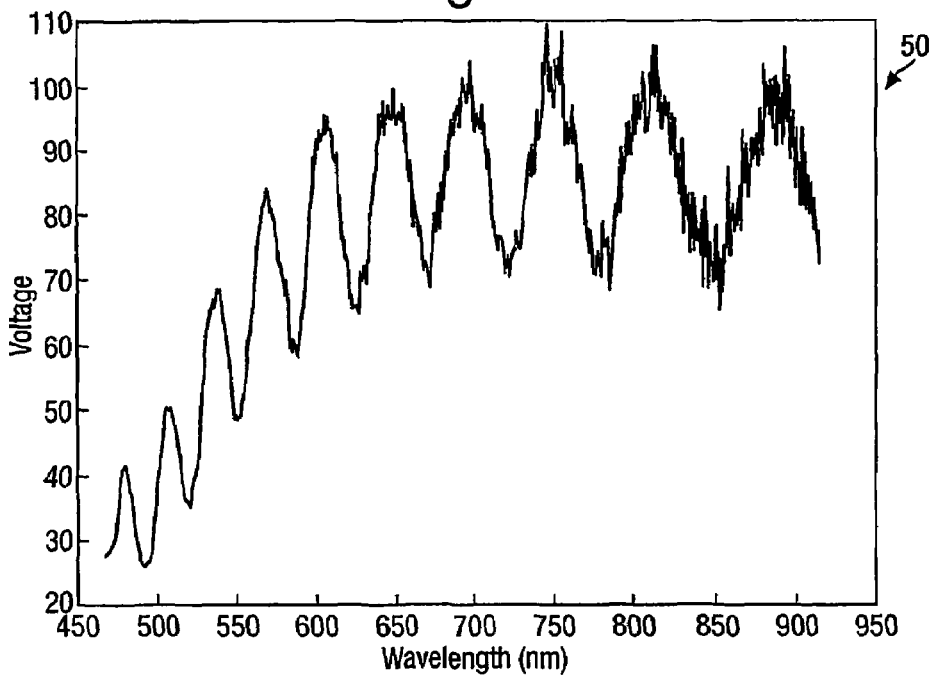
FIG. 2 is a typical interference pattern obtained with the biosensor of FIG. 1.
Figure 3:
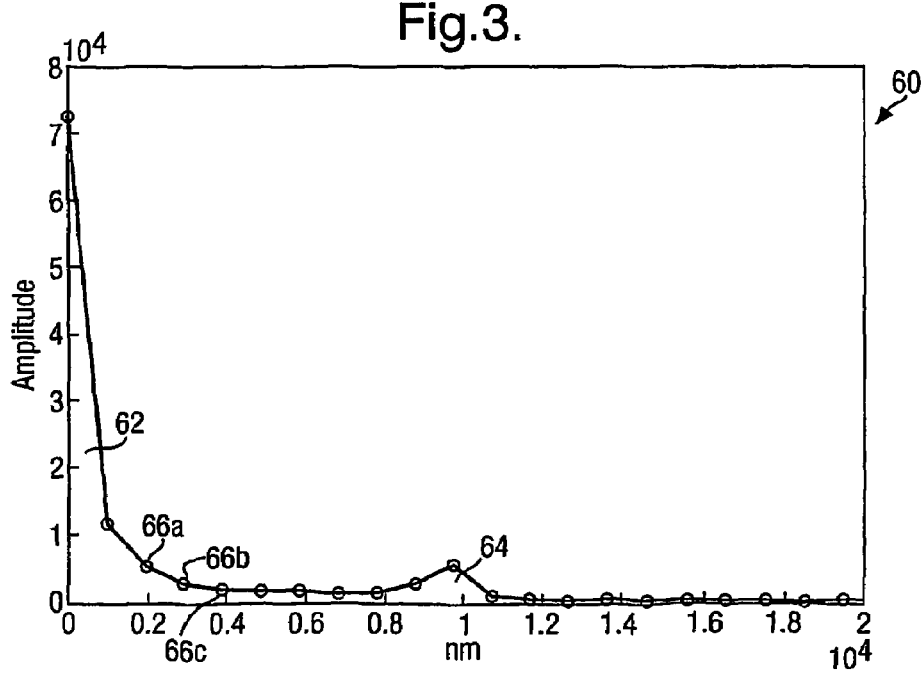
FIG. 3 is a spectrum obtained from the interference pattern of FIG. 2 using a prior art FFT analysis technique.

FIG. 2 illustrates a typical example of an interference pattern 50 generated from the biosensor 10 of FIG. 1. At various wavelengths of light, the voltage developed at the detector 24 is measured. Such measurements contribute to an interference pattern 50 comprising a vector of voltage samples taken at a series of selected wavelengths. Janshoff et al. (referred to earlier) describe one approach to extracting a value of $n_{avg}d$ from such an interference pattern 50. The measured data is first converted to represent a plot of the interference spectrum against the reciprocal of the wavelength (equivalently, wavenumber k) and then the Fourier transform is taken. This transforms the data to a "frequency" domain (in this context use of the word "frequency" refers to the frequency of the peaks in the spectral interference pattern, and not to the frequency of the light used to generate it). A peak in amplitude of the Fourier transform gives a value for the period of the peaks in the original pattern. Janshoff et al. describe use of a fast Fourier transform (FFT) method to generate an interference frequency spectrum from the acquired data points. Following this method, an FFT spectrum 60 of the data shown in FIG. 2 is illustrated in FIG. 3. Two peaks 62, 64 are visible in the transformed data. The larger peak 62 in the region of 0 nm separation values is due to the zero frequency component of the interferogram 50 i.e. the offset apparent in FIG. 2. The smaller peak 64 in the region of 9,500 nm corresponds to a value of $n_{avg}d$, where $n_{avg}$ is the wavelength-averaged value of $n(\lambda_{max})$, which gives rise to the spectral interferogram 50. In addition there is high frequency noise, visible as oscillations superimposed on the interferogram 50 of FIG. 2, but their contribution to the Fourier transform is not visible on the scale of FIG. 3. Sampled data points 66a, 66b, 66c, etc., are also indicated in the plot of FIG. 3. These represent regular sampling points at which the value of the FFT function is calculated. In order to locate the peaks, the interferogram data must be interpolated from the set of wavenumbers k at which detector measurements are made.

Using this approach $n_{avg}d$ can be measured to about 0.5 nm. For a typical layer thickness of 3000 nm, $n_{avg}d$ is about 4000 nm, and so this represents an accuracy of about 1 part in 10 000.

Figure 4:
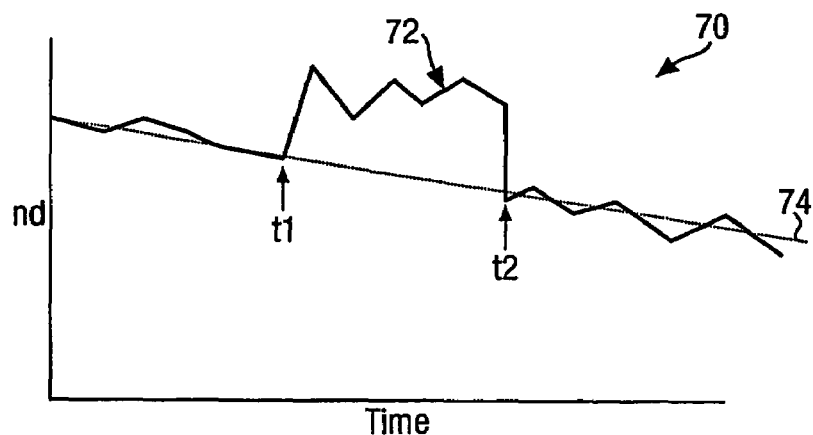
FIG. 4 is a schematic illustration of an idealised result of monitoring optical path difference over time, this result being one which theoretically may be obtained after analysis of a changing interference pattern obtained using the biosensor of FIG. 1.

FIG. 4 illustrates schematically an idealised representation of a set of results which may be obtained using a chemical sensor variant of the biosensor 10 of FIG. 1 and theoretically efficient signal processing. The results are displayed as a plot 70 of the value of $n_{avg}d$ against the time at which each respective spectral interferogram 50 was collected. These idealised readings have been assumed to have been taken with a chemical sensor which does not contain the recognition agent 32 of the biosensor 10. Instead certain molecules introduced into the environment will be simply trapped in the pores of the porous silicon layer. In this, and experiments obtaining actual data which will be referred to later, water is pumped through the sensor 10, which presents a thin film to the flow. Initially the water is pure water, then a sucrose solution is introduced before a return to the flow of pure water. When sucrose molecules are present, they are absorbed into the porous silicon layer.

The plot 70 comprises a series of data points 72 which, on average, follow a sloping background 74. The data points 72 show a clear rise in the value of $n_{avg}d$ at time $t_1$ and a clear drop in its value to the level of the sloping background 74 at $t_2$. The rise at $t_1$ corresponds to the time at which sucrose was introduced into the water being pumped through the sensor 10. As outlined above, sucrose molecules, when present, will be trapped in the porous silicon layer 12. This results in a change in the optical properties of the layer 12 manifest as a change in the value of $n_{avg}d$, in this instance an increase. When sucrose is removed from its environment, and pure water is again pumped through the sensor 10, the trapped sucrose molecules are effectively flushed out and the value of $n_{avg}d$ returns to its original value. Strictly, the value of $n_{avg}d$ falls at time $t_2$ to the projected average background level 74, which in fact is lower than at $t_1$. This reduction in background is a long term drift in the observed level of $n_{avg}d$ it occurs because the porous silicon structure is slightly unstable and is either slowly etched away or oxidised when in solution.

Figure 5:
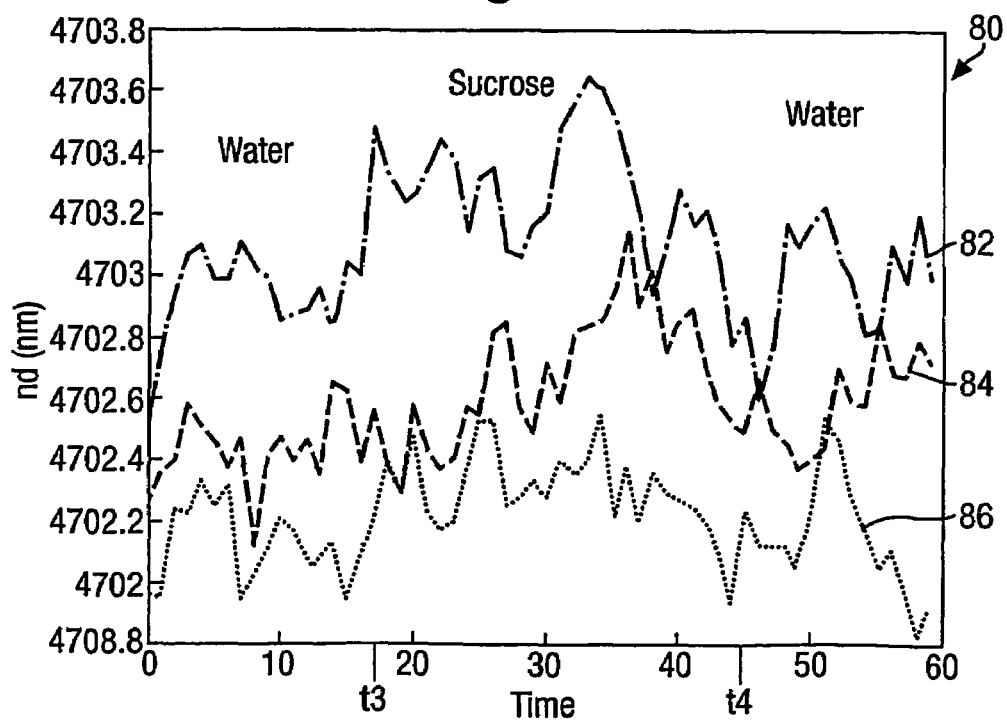
FIG. 5 shows three plots equivalent to that shown in FIG. 4, but extracted by a prior art signal analysis technique from an actual data set obtained using the biosensor illustrated in FIG. 1.

FIG. 5 is a plot similar to that shown in FIG. 4 but taken from an actual set of results obtained using the chemical sensor and water/sucrose solution as described above and analysed using the prior art FFT technique. It gives graphs of optical thickness $n_{avg}d$ (shown as nd) against time: with the equipment used the interferogram scan rate was linear in wavenumber, so the time axis is also a measure of wavenumber. Similar remarks apply to other drawings with time axes.

The results 80 take the form of three separate traces 82, 84, 86 corresponding to pumping sucrose solutions through the sensor film 12, the solutions being 0.1% (upper trace 82), 0.05% (middle trace 84) and 0.03% (lower trace 86) sucrose in water. Points $t_3$ and $t_4$ are marked on the time axis as indicators of the times at which the sucrose solutions were first introduced and then removed from the sensor environment respectively. FIG. 5 shows that it is not possible to detect reliably from the traces 82, 84, 86 when either of the environmental changes—sucrose introduction or removal—occurred.

As noted previously, there are in fact several defects in the application of the FFT analysis method to data obtained from the biosensor 10 of FIG. 1. Data is collected at regular wavelength intervals, which inevitably corresponds to a non-linear series of wavenumbers Analysis therefore requires interpolation of data between regular sampling points in the Fourier transformed spectrum. Interpolation assumes a particular correlation function (e.g. a linear relationship between adjacent samples), which is imposed on the data and which will differ from the true correlation function. Such filtering inevitably distorts the shape of the transformed spectrum. In order to achieve the desired sensitivity in measurement of $n_{avg}d$ to 1 part in 10 000, the position of the desired peak in the FFT spectrum must be determined with an accuracy better than 1/10000th of the width of a Fourier resolution cell. This is very difficult to achieve by interpolating between the points in the FFT spectrum. In addition, the observed interference patterns are not exactly sinusoidal, primarily due to the fact that the refractive index varies with wavelength but also due to some systematic noise in the measurements. The FFT method has been found to be sensitive to this distortion and also to noise. It is clear from FIG. 5 that this prior art technique fails to extract sufficiently clean results from measured interferometric spectra to allow transduction of the molecular trapping, in this instance, to be observed.

Finally, although a simple monolayer biosensor system with only a two-beam reflected interference pattern is described herein, there is no obvious extension of the prior art FFT method to the analysis of more complicated interference patterns obtained from more complex structures, e.g. a multilayer porous silicon structures. These structures give rise to interference patterns which can be far from sinusoidal and accordingly use of a FFT would simply not be of any assistance in their analysis.

By way of contrast to the prior art, the present invention does not rely on interpolation of a Fourier transform spectrum. Nor even necessarily on the Fourier transform technique at all, although in approximately periodic systems there are advantages in making use of it to some extent. There are two stages involved in implementing this invention, and novel aspects of both stages will be described.

In the mathematical analysis which follows, the expression 'function' means a closed form continuous or analytic function, and a set of values (perhaps measurements, results or intermediate results) is represented as a vector such as X having members (vector elements) $X_j$. Such a vector may be used to replace the function, and represent it discontinuously as a set of discrete points such as $X_j$. The term 'entity' is used to mean an item which is a vector member, a vector or a function.

In general, the method of analysis of the invention assumes that a set of discrete observations or measurements is made of an observed variable x, the set being represented by the data vector X. The observed variable x may be regarded as a member of the set X or equivalently as an element of the vector X, and it is derived by measurements upon a physical system characterised by an unknown and variable parameter $\omega$. Each member of X represents a measurement made at a respective value of an interrogation or measurement parameter of the kind k, so that the jth member of X, $X_j=x(\omega, k_j)$. In accordance with the invention, it is assumed that the function x, or $x(\omega, k)$ since it is a function of $\omega$ and k, can be expressed as the sum of an imperfectly known function $f(\omega, k)$ and a random noise process $\eta(k)$, i.e.:

$$x(\omega, k) = f(\omega, k) + \eta(k) \qquad (2)$$

Without affecting the generality of the method of the invention, it is apparent that the detector 24 in the apparatus of FIG. 1 detects a respective voltage at each wavenumber. In this example the parameter $X_j$ may therefore be designated as a detector voltage measured at a particular value of k, which is designated as the wavenumber of that measurement. Upper case X is a vector having vector elements or members which collectively form a set of voltages providing individual points on and used herein to define a whole interferogram.

The interferogram 26 therefore constitutes a set X of individual voltages $X_j$, and each voltage $X_j$ is measured at a respective discrete wavenumber in a wavenumber set. The parameter $\omega$ may therefore be designated as the optical thickness of the porous silicon layer 12 i.e. $n_{avg}d$ when its pores are filled with a solvent. Noise is also included in the method as the parameter $\eta(k)$, which is independent of $\omega$.

It is an important characteristic of the invention that it makes a virtue out of necessity. The invention is directed to detecting perturbations to a physical system manifesting themselves as very small changes to some physical parameter, optical thickness in the present example. The invention exploits the fact that the parameter changes to be detected are very small by using that as a basic assumption in analysing experimental data. In this connection, for small changes in $\omega$ about a reference value $\omega_0$, $f(\omega,k)$ can be expanded about $\omega_0$ and Equation (2) can be rewritten:

$$x(\omega,k) = f(\omega_0,k) + (\omega-\omega_0)f'(\omega_0,k) + \eta(k) + O((\omega-\omega_0)^2) \qquad (3)$$

where $f'(\omega_0,k)$ is the derivative of $f(\omega,k)$ with respect to $\omega$ at $\omega=\omega_0$ and $O((\omega-\omega_0)^2)$ denotes terms of the second and higher orders in $(\omega-\omega_0)$, i.e. $(\omega-\omega_0)^2$, $(\omega-\omega_0)^3$ etc. For small $(\omega-\omega_0)$, the terms $O((\omega-\omega_0)^2)$ can be ignored. If both $f(\omega_0,k)$ and $f'(\omega_0,k)$ can be estimated, then an estimate of the parameter change or perturbation $(\omega-\omega_0)$ between $\omega$ and $\omega_0$ is obtainable from Equation (3) by evaluating:

$$(\omega - \omega_0)_e = \frac{(x(\omega, k) - f(\omega_0, k)_e)}{f'(\omega_0, k)_e} \text{ for any } k. \tag{4}$$

where the subscript e denotes an estimated value.

In order to implement the model represented by Equation (4), two stages are employed, stages 1 and 2. Stage 1 is concerned with finding a reference value $\omega_0$ with respect to which the parameter of interest $\omega$ will be determined as a difference $(\omega - \omega_0)$. Stage 2 relates to evaluating Equation (4) above or an equivalent at specific values of the parameter k: this is in order to determine the parameter change or shift $(\omega - \omega_0)$ from $\omega_0$ caused by a change in this example to the optical properties of the porous layer 12. Initially a vector F is used to denote a set of discrete values or points on the function $f(\omega_0, k)_e$ at values of k defined by $k=k_j$, $j=1$ to $N_k$. Similarly, the vector F' denotes the set of values of the function $f'(\omega_0, k)_e$, at the same set of values of k. To implement stages 1 and 2, two series of data vectors X, i.e. two separate series of interferograms, are obtained: the first such series is a series of calibration data vectors, $X^j_c$, $j=1$ to $N_c$, which defines a background state of the sensor system. The second such series is a series of test data vectors, $X^j_t$, $j=1$ to $N_t$, in which a perturbation manifest as a change in a system parameter is to be measured. Here $N_c$ is the number of calibration data vectors collected, and $N_t$ is the number of test data vectors collected. Typical values in the examples described herein are $N_c=20$, and $N_t=60$. Each interferogram has 1050 points, so each data vector $X^j_t$ has 1050 members $X^j_{ti}$.

Various alternatives are available to provide a reference value $\omega_0$: two such will be described herein with reference to the chemical sensor system of FIG. 1. Clearly many alternative approaches may be used, being somewhat dependent on the nature of the system under analysis and the information available with which to formulate an estimate.

FIG. 6 is a flow chart of an example of steps involved in making the estimates F and F' in applying the present invention to the porous silicon biosensor system of FIG. 1. A first approach to stage 1 of the analysis is represented by steps 90 to 96 of this drawing. Firstly, at 90 a set of calibration data (CD) vectors $X^j_c$, $j=1$ to $N_c$, is collected using the apparatus of FIG. 1. Each vector $X^j_c$ is measured at a different time, and the noise in each measurement (see Equation (2)) will be different. These vectors are obtained by scanning through the measurement wavenumber range several times and recording detector voltages $X_j$ at specific wavenumbers. They are collected while pure water flows through the biosensor 10, and thus are known to be due to a hydrated porous silicon layer 12. Test data vectors $X^j_t$, $j=1$ to $N_t$ taken in biosensor environments other than pure water may be collected at this time. In fact they are ideally collected after one set of calibration data vectors and before another, to provide a two-sided calibration with intervening test. It is found however, that a one-sided calibration (i.e. that performed using data taken either before or after the test measurements) is also effective. In either case, the test data vectors are not subjected to analysis until stage 2 of this analysis system.

In general application of the invention, it is apparent that the actual nature of the calibration data vectors will depend on the system under investigation.

The next step 92 is calculation of an average calibration data vector ($CD_{av}$) from the collected set of CD vectors or interferograms of the kind $X^j_c$. This is carried out by adding the voltages $X_1$ at a first measurement wavenumber $k_1$ on all the calibration interferograms and dividing by the total number. This is then repeated for all other wave numbers. An average interference pattern $CD_{av}$ or average calibration data vector results from this step, and provides a basis for deriving an estimate vector F of the function $f(\omega, k)$ at $\omega = \omega_0$. F has a respective member at each value of $k_j$, $j=1$ to $N_k$.

In analysing the signal from the biosensor system detector 24, the nature of the relationship between variables makes it convenient to use a Fourier transform function in order to derive an estimate of the reference value $\omega_0$. Thus a fast Fourier transform (FFT) spectrum of the average $CD_{av}$ vector is computed at 94 (other spectral analysis techniques may also be used). In this average FFT spectrum, the position and phase $\phi$ of its largest amplitude peak is determined at 96. This position is used to calculate the reference value $\omega_0$, which is the optical thickness of the porous layer 12 when pervaded by a pure solvent, in this case water.

A second approach to stage 1 comprises analysing biosensor signals in a novel manner. It obviates the need for interpolation of an FFT: this is because in certain circumstances it has been found that it is unnecessary to Fourier transform an entire data spectrum. A Fourier transform can instead be calculated directly in a region of interest. This novel analysis component will be referred to herein as a direct Fourier transform.

In application to the biosensor 10, this approach recognises that the approximate optical thickness of the porous silicon layer 12 will be known beforehand from the layer thickness, porosity and solvent type. From this known thickness an expected Fourier transform peak position can be deduced. The Fourier transform peak is not expected to shift significantly in response either to an analyte becoming bound to a recognition agent or a solute molecule becoming trapped in the porous silicon layer 12, because the resulting change in optical properties will normally be too small for this. Accordingly, the Fourier transform can be computed directly for a series of optical thickness values in a predetermined range of such values: the range is centred on the optical thickness value which corresponds to the expected location of the Fourier transform peak. Estimates of the peak position are fine-tuned by use of a line search or iterative peak finding position. An important advantage of this example is that it does not use interpolation. Instead the Fourier transform is computed at a set of data points in the region of interest directly from the collected data, i.e. at data points instead of between them so interpolation error does not arise.

Figure 7:
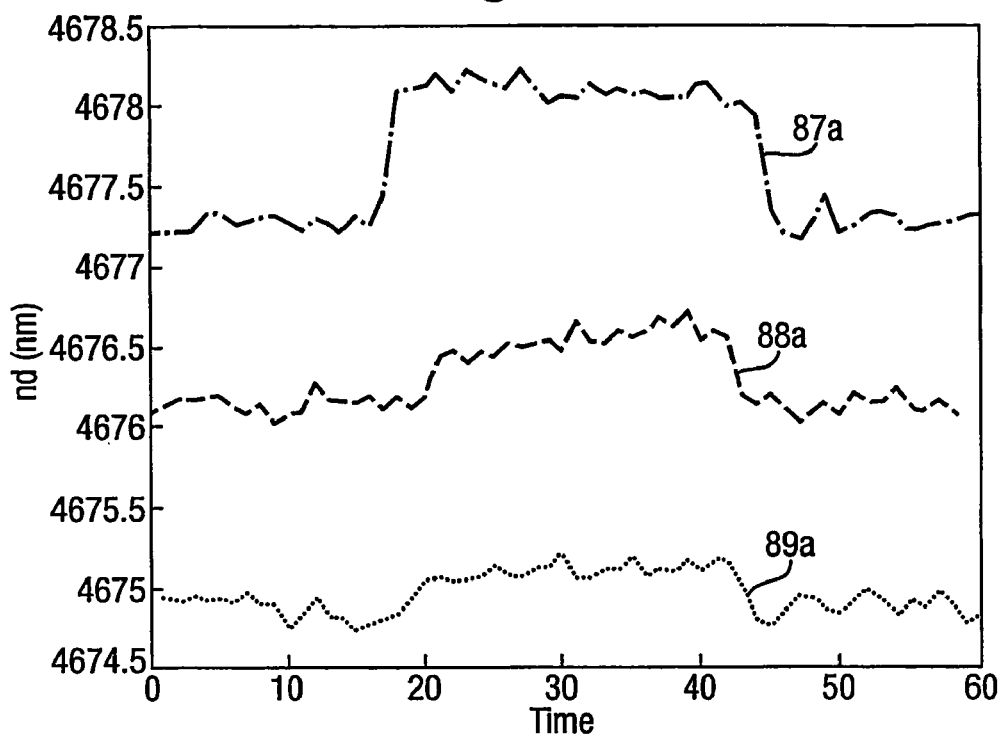
FIG. 7 illustrates spectra equivalent to those shown in FIG. 5, this time obtained using a first stage of the present invention.
Figure 8:
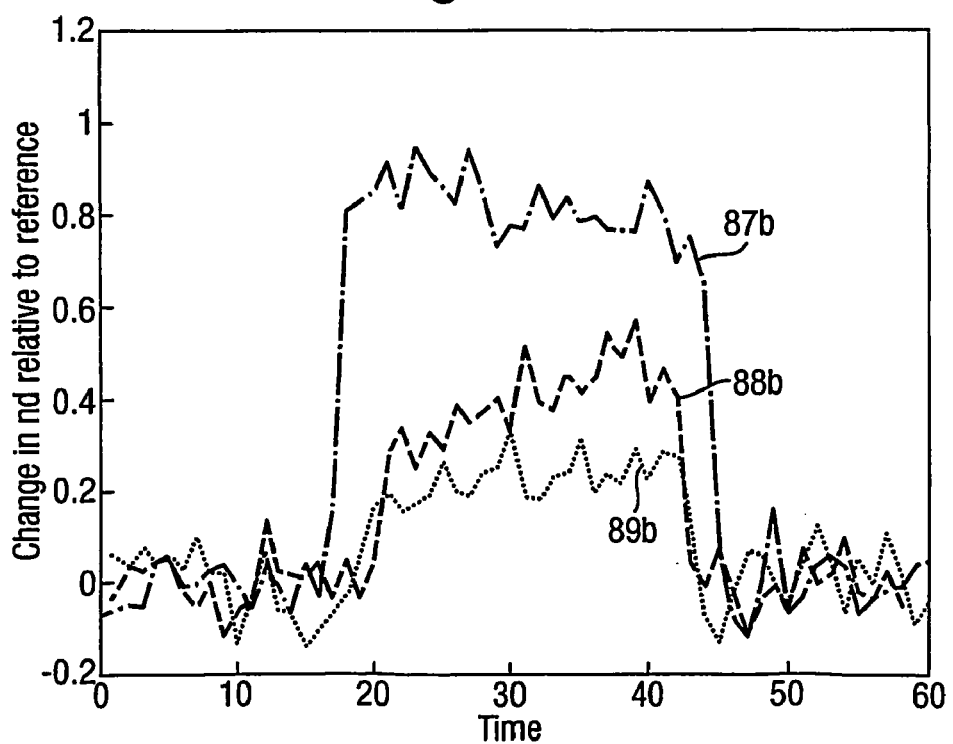
FIG. 8 is a rescaled version of the plots of FIG. 7.

Each interference pattern detected by the biosensor system of FIG. 1 and used in the derivation of the traces shown in FIG. 5 has been analysed using the above-described direct Fourier transform method. That is, for each data vector, the peak position (and hence value of $n_{avg}d$) has been extracted using this method of analysis of the invention instead of the prior art FFT technique. FIGS. 7 and 8 display the results of this analysis: FIG. 7 illustrates three traces 87a, 88a and 89a of $n_{avg}d$, again corresponding to immersion of the sensor 10 in pure water (background calibration over times 1 to 16 and 45 to 60) and in various sucrose solutions (measurements over times ~20 to ~45). For the plots 87a, 88a and 89a, the sucrose solutions are 0.1%, 0.05% and 0.03% sucrose in water respectively. FIG. 8 illustrates three traces 87b, 88b, 89b obtained by dividing each of 87a to 89a of FIG. 7 by a respective mean background value, i.e. in each case the mean of the values obtained over times 1 to 16 and 45 to 60. It can be seen from FIGS. 7 and 8 that a distinct improvement is immediately apparent over the prior art analysis system used to generate the results shown in FIG. 5. Moreover, it is further clear that in the cases of all three solution strengths, a threshold can be set which will distinguish between water and sucrose environments. It is to be noted that this improvement was effected by implementing stage 1 of this invention only.

Note that it is not essential to use a Fourier transform at this stage. All that is required is a method of determining the initial reference value $\omega_0$. Thus signals from other perturbed physical systems may be amenable to other forms of analysis. Two embodiments of stage 1 have been described herein however in relation to an approximately periodic interference signal, and accordingly Fourier transforms have been used for convenience.

The second, novel, stage of this analysis technique arises from recognition that in many systems, it is not necessary to measure an absolute value of a parameter for every configuration: instead it is enough to establish an approximate reference or background value and then to measure variations about this reference. That is, this stage is applicable whenever variations in an observed parameter can be seen as perturbations relative to a reference value of that parameter. It is accordingly to be noted that it is relevant to many perturbation detection applications, and not merely to analysis of roughly periodic signals. For convenience however, roughly periodic signals will continue to be used as illustrative examples herein.

Using this analysis technique, parameter variations are extracted directly. It is therefore unnecessary to calculate the Fourier transform, provided that some other way is available to generate a reference signal. In particular, it is not necessary to make the assumption that the signal being detected is a pure sine wave, that assumption being inherent in the Fourier transform technique. This leads to an improved signal to noise ratio in the processed signal and consequently, better detectability of event thresholds.

There will now be described the steps involved in deriving the estimates F and F' for use in deriving an error vector E with a jth member $E_j$. This employs Equation (5), which is obtained by evaluating Equation (4) at each value of $k=k_j$, $j=1$ to $N_k$:

$$E_j = (\omega - \omega_0)_e = \frac{(X_{tj} - F_j)}{F'_j}. \qquad (5)$$

Ideally the estimates F and F' (with jth values $F_j$ and $F_j'$) are obtained from a number of data vectors (interference pattern value sets): they are then weighted according to their signal to noise ratios and averaged, although it is believed that such weighting would make the system more sensitive to the uncertainty in knowing $f'(\omega_0,k)_e$.

Referring once more to FIG. 6, and as described earlier, by Step 96 a value and phase $\phi$ for the reference value $\omega_0$ has been derived in stage 1 of the analysis technique. The range of optical thicknesses expected to be encountered using the biosensor 10 is known, and therefore the range of interferogram peak positions expected is also known. A range of discrete values of $\omega$ spanning this thickness range and centred on $\omega_0$ is selected at 98 and a corresponding set S of sinusoidal data vectors is generated. For this purpose parameters of the kind $\delta\omega_1$ are defined which are offsets expressing the range of discrete values of $\omega$ as individual offsets from $\omega_0$. This provides a set of sinusoidal functions $s(\omega_l,k_j)$ given by:

$$\{s(\omega_l,k)\}=\{\sin((\omega_0+\delta\omega_l)k+\phi)\} \qquad (6)$$

where $\{\}$ indicates a set, $\delta\omega_l$ is the lth in a set of offsets $\{\delta\omega_l\}$, each offset may be positive or negative and represents a relatively ($<\frac{1}{10}$) small departure from $\omega_0$, and $\phi$ is the phase of the reference value, as referred to above. The corresponding set S of sinusoidal data vectors is obtained by evaluation of these functions $s(\omega_l,k_j)$ at each value of $k=k_j$, $j=1$ to $N_k$ according to Equation (7)

$$S=\{S^l\}:S_j^l=\{s(\omega_l,k_j)\} \qquad (7)$$

Once more, the selection of sine waves is specific to the nature of the interference pattern for which there is sought a reference function estimate, $f(\omega_0,k)_e$ evaluated at each value of $k_j$, $j=1$ to $N_k$ to give a reference vector F. The biosensor 10 is assumed to give rise to an interference pattern which is an approximate cosine function, so a reference vector for such a pattern will have the form of a set of discrete points on such a function. The method of the invention detects perturbations with respect to the reference vector, i.e. small departures from the reference vector: such departures will be associated with the reference derivative vector, sine functions in this example.

At step 100 the calibration data is filtered using the set S. That is, each observation or measurement vector $X_c^j$, $j=1$ to $N_c$, made in collecting the calibration data vectors (interference patterns), is assumed to be a respective linear combination of all members of the set S. This treats each $X_c^j$, $j=1$ to $N_c$, as being projected on to each sinusoidal data vector in the set S acting as a basis vector in each case. Components in the direction of each sinusoidal data vector in S are therefore computed for each observation vector $X_c^j$, $j=1$ to $N_c$. This step 100 produces filtered calibration data ($CD^f$) which again is averaged as described earlier at a following step 102 to produce an estimate of the imperfectly known reference data vector, F in terms of the reference value $\omega_0$ and the set of offsets $\{\delta\omega_l\}$ The filtering removes explicit dependence upon the interrogation parameter or wavenumber k: that is, the observation vector X has been transformed from k space to a projected observation vector Z in the space of the sinusoidal data vectors, with their dependence on selected (discrete) values of $\delta\omega$, according to Equation (8):

$$Z_l = z(\omega, \delta\omega_l) = \sum_j x(\omega, k_j)\sin((\omega_0 + \delta\omega_l)k_j + \phi) \qquad (8)$$

Equation (8) represents the lth member $Z_l$ of the projected observation vector Z as taking the value $z(\omega,\delta\omega_l)$ at $\delta\omega=\delta\omega_l$; each value $z(\omega,\delta\omega_l)$ (general value l) is in turn a respective summation $$\sum_j x(\omega, k_j)\sin((\omega_0 + \delta\omega_l)k_j + \phi)$$

over products of a (jth) member $x(\omega,k_j)=X_j$ of the observation vector X with a respective (lth) member $\sin((\omega_0+\delta\omega_l)k_j+\phi)$ of the set S of sinusoidal data vectors. Each projected observation vector Z corresponds to a respective observation vector X.

At step 102 the projected observation vectors Z corresponding in the manner described above to the calibration data (CD) constitute the filtered calibration data ($CD^f$). Then F is computed by adding up respective members of each projected observation vector $Z^j_c$, and dividing the total by the number of such vectors, $N_c$, according to Equation (9):

$$F_l = \sum_{j=1}^{N_c} z^j(\omega, \delta\omega_l)/N_c \qquad (9)$$

where again $F_l$ denotes the lth member of the data vector F, and $z^j(\omega,\delta\omega_l)$ is the lth member of the jth projected calibration data vector $Z^j_c$, evaluated at $\delta\omega=\delta\omega_l$. Thus Equation (9) establishes F for use as the reference vector in Equation (5). The reference vector F, a series of discrete values derived for each value of at $\delta\omega=\delta\omega_j$, j=1 to 2m+1, is now used to represent the estimated reference function $f(\omega_0,\delta\omega)_e$, a continuous function.

FIG. 9 is a flow chart of process steps for direct extraction of the value of the parameter $\omega$ from successive test data vectors $X^j_t$, j=1 to $N_t$, once the reference vector F has been established following a route similar to that outlined with reference to FIG. 6. In FIG. 9, at a first step 110, test or 'real' data RD is acquired in the same way as described earlier for calibration data CD, except that real data is obtained with a small amount of sucrose present in the otherwise pure water solvent. The real date RD is filtered using the set of sinusoidal data vectors S, as defined in Equation (7). That is, each measurement is again assumed to comprise a linear combination of members of the set S. The set S does not contain high and low frequency terms, and so both high and low frequency noise are suppressed in the filtered real data. Subsequent processing is performed on real data $RD^f$ filtered in this way. The filtering step 110 is not essential but it improves signal to noise ratio. At step 112, the reference vector F is subtracted from each data vector $Z^j_t$, for each for each j, j=1 to $N_t$ of the filtered real data $RD^f$: this subtraction provides a difference vector which is the error vector $E^j$, for each j, j=1 to $N_t$, i.e. a respective error vector is derived for each test interferogram. From Equation (5), it can be seen that each member of the error vector is proportional to $(\omega-\omega_0)$.

Figure 10:
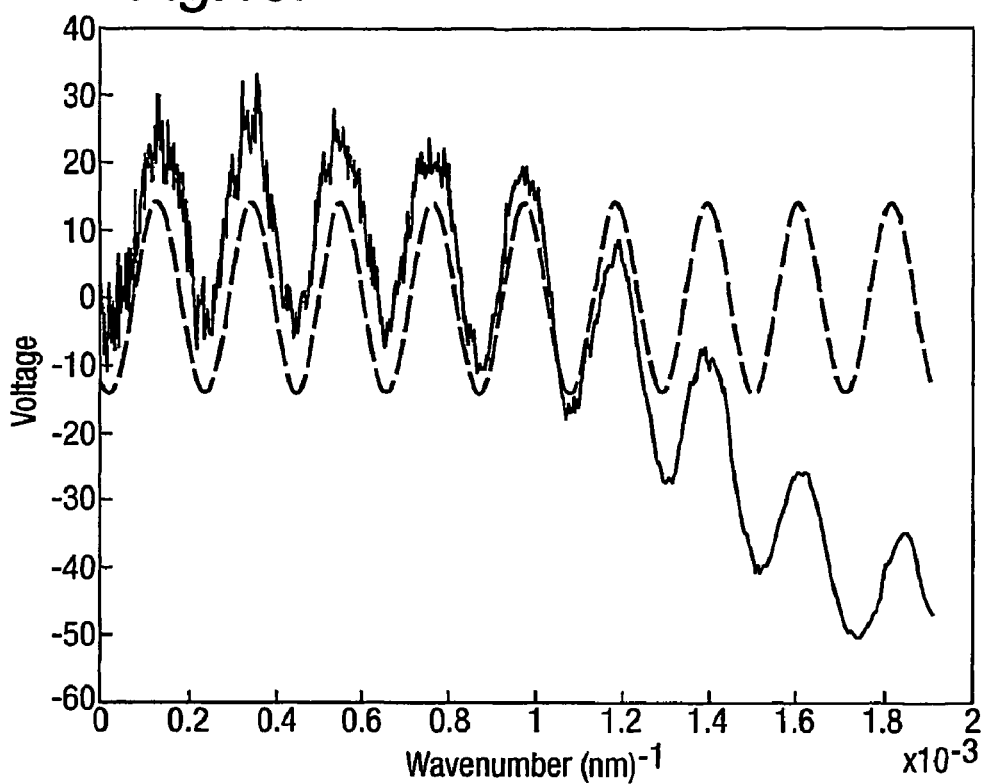
FIG. 10 provides graphs of an estimated reference function $f(\omega_0, k)_e$ and a $\cos(\omega k)$ approximation to it plotted against wavenumber in each case.

It is now assumed that (before projection on to $\{s(\omega_l,k)\}$, and never explicitly computed) the estimated reference function $f(\omega_0,k)_e$ is of the form $\cos(\omega k)$. That this is reasonable approximation is illustrated in FIG. 10, where the estimated reference function $f(\omega_0,k)_e$ is plotted as a function of wavenumber k (solid line) compared to a $\cos(\omega k)$ approximation (dashed line). The derivative of $\cos(\omega k)$ with respect to $\omega$, i.e.

$$\frac{\partial}{\partial \omega}\cos(\omega k),$$

is $k \sin(\omega_0 k)$ when evaluated at the reference point $\omega_0$. This estimated derivative function is denoted $f'(\omega_0,k)_e$, and when evaluated at each value of $k=k_j$, j=1 to $N_k$ yields the derivative vector F'.

In order to make a proper interpretation of small differences between a projected observation vector Z and a projected reference vector F, the derivative vector F' is also projected at step 114 onto the set of sinusoidal data vectors S of Equation (7) to give members of F' as follows:

$$F'_l = \sum_j f'_j(\omega_0, k_j)_e \sin((\omega_0 + \delta\omega_l)k_j + \phi) \qquad (10)$$

where again $F_l'$ denotes the lth member of the derivative vector F'.

Figure 11:
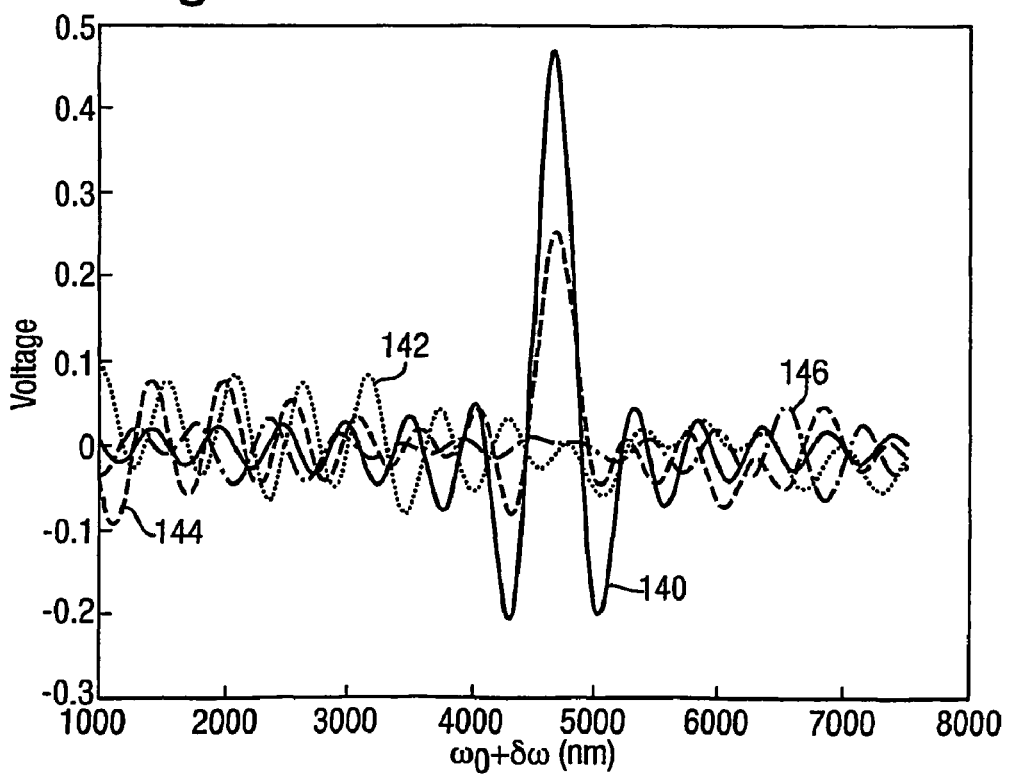
FIG. 11 provides graphs of error functions plotted against wavelength.
Figure 12:
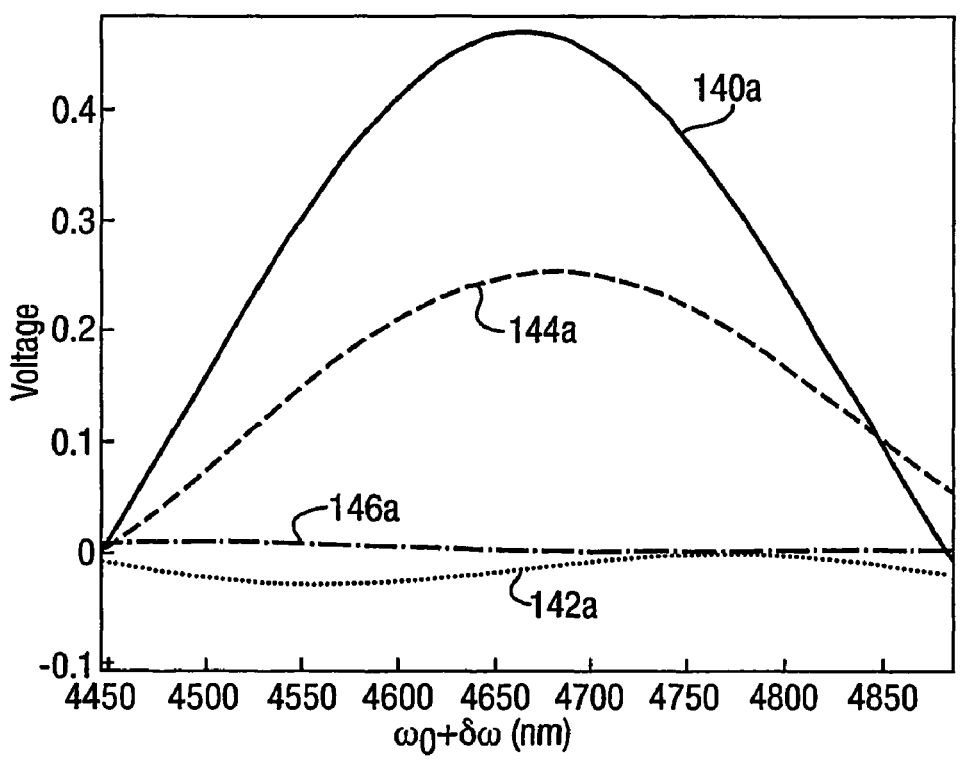
FIG. 12 shows regions of the FIG. 11 graphs at a peak of one of the graphs.

Referring now to FIG. 11, the vector F' represents the projected estimated derivative function $f'(\omega_0,\delta\omega)_e$, evaluated at each value of $\delta\omega=\delta\omega_j$, j=1 to 2m+1. The function $f'(\omega_0,\delta\omega)_e$ represented by F' is shown as a solid curve 140 plotted as a function of $\omega_0+\delta\omega$: it is a $\mathrm{sinc}(\omega_0+\delta\omega)$-like function, i.e. it is of the form $(\sin\theta)/\theta$. It is compared to similar plots 142 (dots), 144 (dashes) and 146 (dash-dot) for three error functions of the form $e(\omega,\delta\omega)$, which when evaluated at each value of $\delta\omega=\delta\omega_j$, j=1 to 2m+1, are represented by the error vectors E. The plots 142, 144 and 146 are taken respectively from a preceding calibration interval (interval from times 1 to 16 in FIG. 8) the measurement interval (times 20 to 40 in FIG. 8) and a second calibration interval (times 48 to 60). The plot 140 has a peak 140a shown in FIG. 12, in which like located regions 142a to 146a are also shown. The error functions $e(\omega,\delta\omega)$ are equal to the numerator of Equation (4), i.e. to $(x(\omega,k)-f(\omega_0,k)_e)$, and from that equation they are also equal to $f'(\omega_0,k)_e(\omega-\omega_0)_e$. From this it can also be seen that if the functions $f'(\omega_0,k)_e$, $x(\omega_0,k)_e$ and $f(\omega_0,k)_e$ are all projected on to the sine function space $\{s(\omega_l,k)\}$ removing the dependency on wavenumber k, then:

$$e(\omega,\delta\omega)=f'(\omega_0,\delta\omega)_e(\omega-\omega_0)_e=x(\omega,\delta\omega)-f(\omega_0,\delta\omega)_e \qquad (11)$$

is true for all values of $\delta\omega$. This means one can also combine results for all values of $\delta\omega$ by integrating Equation (11). Thus, integrating and dividing both sides of Equation (11) by $\int f'(\omega_0,\delta\omega)_e$:

$$(\omega-\omega_0)_e = \frac{\int e(\omega,\delta\omega)}{\int f'(\omega_0,\delta\omega)_e} = \frac{\int (x(\omega,\delta\omega)-f(\omega_0,\delta\omega)_e)}{\int f'(\omega_0,\delta\omega)_e} \qquad (12)$$

Moreover, summation over a subset of the $\delta\omega$ values in the originally-selected range of interest (that surrounding $\omega_0$) will also hold true. It is not essential to carry out a summation, any member of an error vector can be used to provide an estimate $(\omega-\omega_0)_e$, but summing over a number of selected low noise members improves accuracy for the usual statistical reasons. Thus, converting continuous functions in Equation (12) to data vectors and integrals to summations over their members:

$$(\omega-\omega_0)_e = \frac{\sum E}{\sum F'} = \frac{\sum X - F}{\sum F'} \qquad (12a)$$

where the summations are of vector members corresponding to a subset of $\delta\omega$ values chosen as follows: the chosen subset comprises those $\delta\omega$ values for which the respective associated values of the error function are large relative to residual noise. Error function values are large over the peak 140a of the sinc function $f'(\omega_0,\delta\omega)_e$ at 140. Therefore, at step 116 (FIG. 9) a summation is made of values of the error function $e(\omega,\delta\omega)$ at values of $\delta\omega$ that span the sinc peak 140a. This corresponds to summing appropriate members of the error vector E for an interferogram, since, as previously explained, each member of E, $E_j$ is equal to the value of the function $e(\omega,\delta\omega)$ evaluated at the value of $\delta\omega=\delta\omega_j$, j=1 to 2m+1.

In this example of the invention, an interferogram and the data vector X which represents it has 1050 measurement points/members, and error vector members corresponding to 101 these points are selected for summation. The sinc peak 140a occurs at about 4650 nm corresponding to $\omega_0$. It is about 700 nm wide, and requiring 101 points spread over approximately the upper half of the peak 350 nm wide (full width half maximum) gives $\delta\omega$ values with a spacing of 3.5 nm. The general value of $\delta\omega$, i.e. $\delta\omega_j$, is then given to be a wavelength increment or decrement of (3.5(j−1)−175) nm. The maximum value of $\delta\omega$ is approximately $\omega_0/27$; $\delta\omega$ is therefore no more than relatively small compared to $\omega_0$, less than one tenth of it.

The summation over the sinc peak 140a provides the numerator of the right hand side of Equation (10). It gives an indication that $\omega$ has changed, but not the absolute value of that change. For many purposes such an indication is all that is needed, such as for example when an alarm signal is required to indicate a change from a required state has occurred.

It is an important property of the invention that signal to noise ratio can be improved as described by only using relatively large values of error functions and discarding those with poorer signal to noise ratios.

To provide an absolute value of the shift in $\omega$ using Equation (12a), rather than just an indication that it has changed, the normalisation factor $\Sigma F'$ in the denominator of the right hand side of that equation is required. At step 118, $\Sigma F'$ is evaluated and applied as follows. It is equivalent to evaluating the function $f'(\omega_0,\delta\omega)_e$ for $\delta\omega$ in the chosen subset of $\delta\omega$ values referred to above, these function values being summed. This corresponds to summing appropriate members of F', since, as was previously explained, each member of F', $F_j'$ is equal to the value of $f'(\omega_0,\delta\omega)_e$ evaluated at $\delta\omega=\delta\omega_j$, j=1 to 2m+1. The summation is performed over the subset of $\delta\omega$ values over which members $E_j$ of the error vector E were summed. The sum of the error vector values (numerator on the right hand side of Equation (12a)) is then divided by the resulting normalisation factor $\Sigma F'$ to give $(\omega-\omega_0)$, and hence $\omega$ itself as $\omega_0$ is known.

There are a number of enhancements which may be added to the analysis described above. The first enhancement concerns random amplitude fluctuations which appear in the interference patterns. See, for example, the pattern shown in FIG. 2. Referring to FIGS. 6 and 9 once more, in this enhancement the subtraction at step 112 is replaced by a projection. That is, instead of deriving the error function $e(\omega,\delta\omega)$ by subtracting $f(\omega_0,\delta\omega)_e$ from each filtered interference pattern using Equation (11), each filtered pattern is projected onto a space orthogonal to that of F, the reference vector. This calculation is equivalent to normalising each projected data vector Z by dividing by an estimate of the unknown amplitude of each projected data vector Z and then subtracting F.

Secondly, in place of the static reference function $f(\omega_0,\delta\omega)_e$, at steps 102 and 112 a linearly time-varying reference function $f(\omega_0,\delta\omega,t)_e$ is used, where t is time. This will be described in terms of functions for convenience, although strictly speaking it should be in terms of data vectors as described earlier for the time-invariant case. It is achieved by assuming the calibration data follows a best-fit slope over time, and this is taken into account at the averaging step 92. The time-varying reference function or estimated interference pattern $f(\omega_0,\delta\omega,t)_e$ is consequently defined to be the sum of the static reference function $f(\omega_0,\delta\omega)_e$ computed from Equation (9), and a linearly time-varying pattern $v(\omega_0,\delta\omega)_e$ calculated from Equation (13).

$$v(\omega_0, \delta\omega)_e = \frac{\left(\sum_{j=1}^{N_c}(j-(1+N_c)/2)(z^j(\omega,\delta\omega)-f(\omega_0,\delta\omega)_e)\right)}{\left(\sum_{j=1}^{N_c}(j-(1+N_c)/2)^2\right)} \quad (13)$$

In Equation (13), $N_c$ is the number of observation data vectors $X_c$ obtained in calibration. This Equation shows that the function $v(\omega_0,\delta\omega)_e$ is obtained by subtracting $f(\omega_0,\delta\omega)_e$ from $z^j(\omega,\delta\omega)$, which is the member of the jth projected calibration data vector $Z^j$ corresponding to $\delta\omega$, for each value of j from 1 to $N_c$, scaling the each resulting difference by multiplying by the current value of $j-(1+N_c)/2$, and then adding up all the scaled differences. The resulting total is divided by the sum of the squares of the values of $j-(1+N_c)/2$. Equation (14) is then used to compute $f(\omega_0,\delta\omega,t)_e$:

$$f(\omega_0,\delta\omega,t)_e = f(\omega_0,\delta\omega)_e + tv(\omega_0,\delta\omega)_e \quad (14)$$

Computer software implementing this embodiment of the invention (i.e. including both the enhancements described above) was developed using "Matlab®" produced by Mathworks Inc., an American corporation. This software is attached at Annex A. It clearly demonstrates that equations given in the foregoing description can be evaluated by an appropriate computer program recorded on a carrier medium and running on a conventional computer system. Such a program is straightforward for a skilled programmer to implement without requiring invention, because the code exemplifies the equations and the equations themselves are well known computational procedures.

Figure 13:
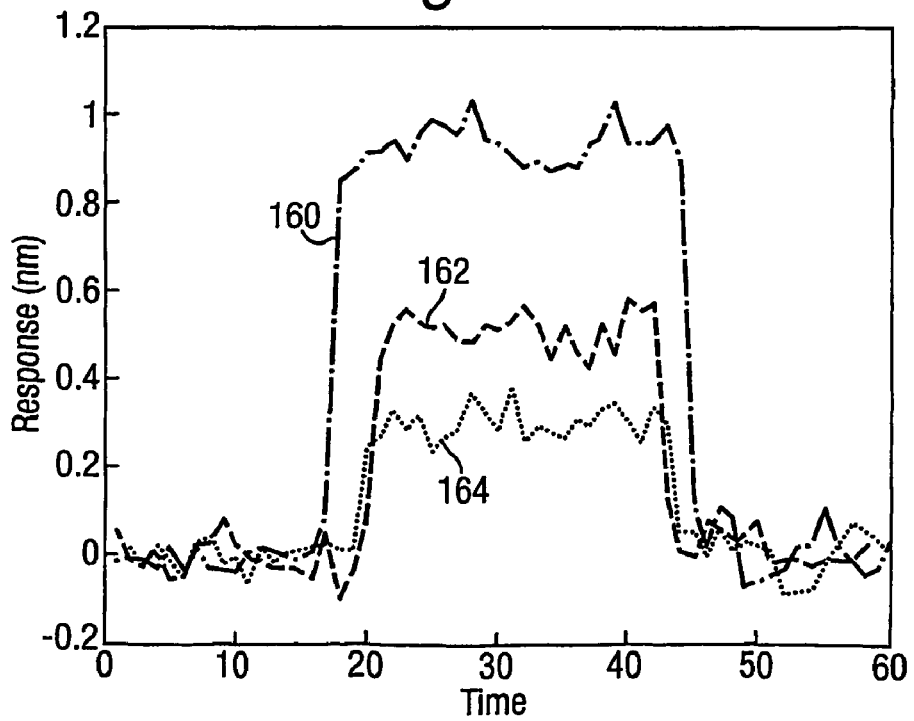
FIG. 13 illustrates spectra equivalent to those plotted in FIGS. 5 and 7, except that two stages of processing in accordance with the invention were employed.

FIG. 13 is an illustration of spectra similar to those plotted in FIGS. 5, 7 and 8, but now obtained using the above-described enhanced analysis technique. This drawing shows three plots 160, 162 and 164 of the kind described earlier: i.e. optical thickness is plotted against time (wavenumber) for three different sucrose solutions with compositions previously given. The plots 160, 162 and 164 exhibit far more pronounced discontinuities when the sensor is exposed to or washed free of the respective sucrose solutions (see times 15-20 and 42-45) than the equivalent in FIGS. 5, 6 and 8.

Although described herein in relation to detection of events using a biosensor, it is to be understood that perturbation detection according to this invention is susceptible to far wider application. It should prove useful in any application in which it is necessary to detect small changes in the response of a sensor and where conventional high-resolution methods fail because of uncertain calibration. One possible application is to laser vibrometry.

It will be apparent to one skilled in the art that the algorithm used in this analysis system can be modified for use with interference (or other) patterns which are not simple sinusoids. All that is needed is to obtain an estimate of a state of a system in terms of a parameter of interest and its derivative with respect to that parameter. This provides $f(\omega_0,k)_e$ and $f'(\omega_0,k)_e$ or equivalents thereof and sets the projection space, and then the same strategy applies.

Figure 14:
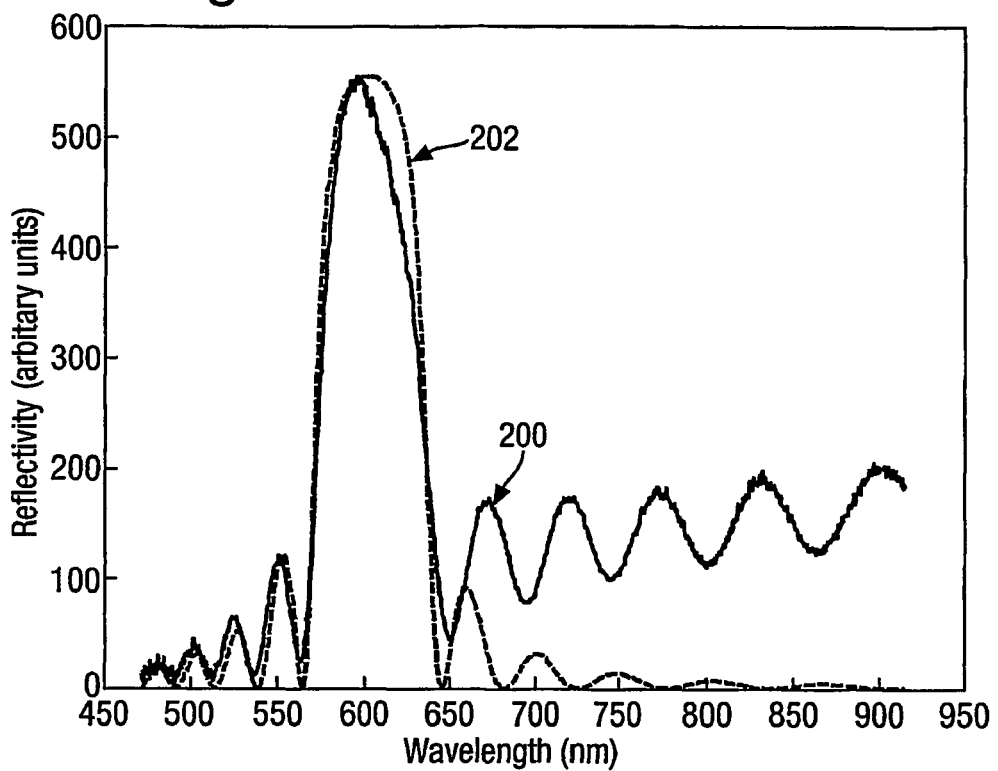
FIG. 14 shows measured and calculated interference patterns obtained using porous silicon sensor with eighteen layers and forming a Bragg mirror.

Referring now to FIG. 14, there are shown two interference patterns indicated generally by 200 (solid curve) and 202 (chain curve) respectively. The patterns 200 and 202 show reflectivity plotted against wavelength in nm. The pattern 200 was measured as described with reference to FIG. 1, except that the single porous silicon layer 12 was replaced by a sensor film of porous silicon having eighteen layers and configured as a Bragg mirror. Each layer consisted of first and second films with different porosities, so the sensor film was effectively thirty-six films or layers in which porosity alternated between two values in successive layers. In other respects the sensor film was illuminated with light and the interference pattern 200 was detected as described earlier. The pattern 200 was obtained while pure water was passed through the sensor film: it provides a reference spectrum and was derived by averaging data in calibration mode.

The pattern 202 was calculated as a reflectivity predicted by a simple analytic model for the sensor film referred to above. For this multilayer sensor film the sensed parameter is a wavelength $\lambda_0$ at which a peak of a spectrum occurs, and an interrogation parameter is provided by illuminating light wavelength $\lambda$ incident on the film. Although it does not provide a perfect fit to pattern 200, the model pattern 202 is sufficiently accurate for use to provide an acceptable approximation to $f'(\lambda_0,\lambda)_e$, which serves the same purpose as $f'(\omega_0,k)_e$ in Equation (4). The model pattern 202 is $f(\lambda_0,\lambda)_e$, and it can be shown that it is described by Equation (15) below:

$$f(\lambda_0,\lambda)=K^2 \sin h^2(y)/(\Gamma^2 \cos h^2(y)+\delta^2 \sin h^2(y)) \quad (15)$$

where $K=2(n_1-n_2)/\lambda$,
$\delta=(\pi/L)(2(d_1n_1-d_2n_2)/\lambda-1)$
$\Gamma=\sqrt{K^2-\delta^2}$
$L=d_1+d_2$, is the thickness of each layer (film thicknesses $d_1$ and $d_2$ having different refractive indices $n_1$ and $n_2$),
$d_1=\lambda_0/(4n_1)$, is the thickness of the first film (quarter wavelength at $\lambda_0$),
$d_2=\lambda_0/(4n_2)$, is the thickness of the second film (quarter wavelength at $\lambda_0$),
$n_1$ is the refractive index of the first film,
$n_2$ is the refractive index of the second film,
$y=mL\Gamma$, and
m is the number of layers in the multilayer sensor, i.e. m=18 in this example.

By differentiating the model pattern 202 with respect to $\lambda$ at $\lambda_0$, $f'(\lambda_0,\lambda)_e$ is obtained as defined in Equation (16)

$$f'(\lambda_0,\lambda) = \frac{(4\pi\delta K^2\sinh(y)/\lambda)(\sinh(y) - mL\Gamma\cosh(y))}{(\Gamma^2\cosh^2(y) + \delta^2\sinh^2(y))^2} \quad (16)$$

Referring to FIG. 6 once more, the multilayer sensor data is processed in the same way as that from a single layer sensor, except that instead of steps 94 and 96 the wavelength $\lambda_0$ corresponding to the peak of the average interference pattern is computed. In step 98 a set P of basis vectors is computed by evaluating a set of functions of the form $p_l(\lambda_0-\delta\lambda_l,\lambda)=f'(\lambda_0-\delta\lambda_l,\lambda)_e$ at discrete values of $\lambda$ and $\delta\lambda_l$, where $\delta\lambda_l$ is the lth in a series of small wavelength changes. In step 100 the calibration data is filtered using P, in the manner described in Equation (10), where $p_l(\lambda_0-\delta\lambda_l,\lambda_j)$ replaces $\sin((\omega_0+\delta\omega_l)k_j+\phi)$. In step 102 $f(\lambda_0,\delta\lambda)_e$ is computed by projection instead of $f(\omega_0,\delta\omega)_e$.

Likewise in FIG. 9 at step 110 the basis set P is used instead of S. At step 112 $f(\lambda_0,\delta\lambda)_e$ is subtracted instead of $f(\omega_0,\delta\omega)_e$, to give $e(\lambda_0,\delta\lambda)$. At step 114 $f'(\lambda_0,\lambda)_e$ is projected on to P to obtain $f'(\lambda_0,\delta\lambda)_e$, which is sinc-like. In step 116 components of $e(\lambda_0,\delta\lambda)$ are summed, and in step 118 the result is normalised to provide an estimate of $\lambda_0+\delta\lambda$, indicating the required shift.

In this example a model pattern was calculated as for the pattern 202 to estimate responses to levels of sucrose dissolved in water.

Figure 15:
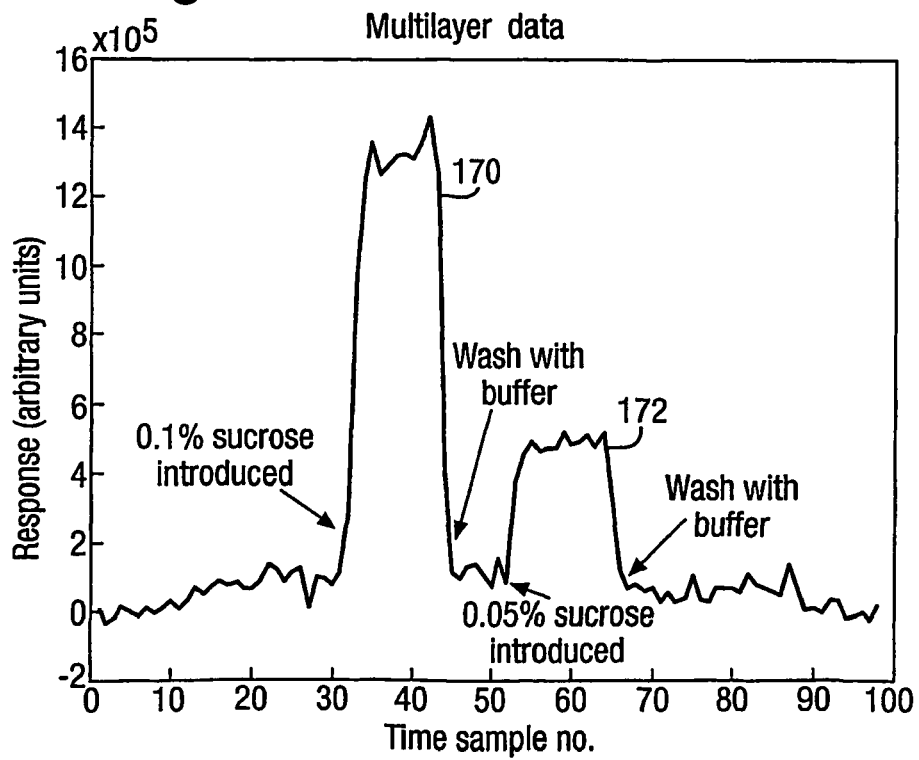
FIG. 15 is a graph of response of the multilayer sensor processing system used to obtain the patterns shown in FIG. 14, and is plotted against time sample number.

FIG. 15 is a graph of response (arbitrary units) of the multilayer sensor processing system described above against time sample number (equivalent to time and wavenumber). Peaks 170 and 172 indicate the response of this system to different concentrations of sucrose in water, 0.1% and 0.05% respectively. The use of a multilayer porous silicon film is advantageous in this application as the reflectivity and consequently the signal to noise ratio is improved as compared to the single layer film, allowing a more sensitive measurement system to be constructed.

```
Annex A MATLAB code
% Script to read in psi experiment data; generate a
time-varying estimate
% of the mean water spectrum and subtract it from each
snapshot vector
% in turn. Then correct for amplitude fluctuations.
% NB graphics removed
% read in data from files
% 0.1% sucrose
%filename='data010.txt'
%outfile='output010.txt'
%n=60;
%plot_title='0.1% sucrose';
% 0.05% sucrose
%filename='data005.txt'
%outfile='output005.txt'
%n=58;
%plot_title='0.05% sucrose';
% 0.03% sucrose
filename='data003.txt'
outfile='output003.txt'
n=60;
plot_title='0.03% sucrose';
% assume the data has two regions of calibration data
w1=17; % last calibration sample in first block
w2=50; % first calibration sample in second block
w3=n; % last calibration sample in second block
% computation options
op1=0; % one sided calibration; op1=0 => two sided
calibration
op2=1; % compute time-varying reference; op2=0 =>
fixed reference
Xa=read_data(filename,n+1);
% separate the data
D=Xa(:,2:n+1);
% from the wavelength (nm) info, and convert to
wavenumber in nm^-1
t=1.0./Xa(:,1);
t=t-min(t);
% since the waveforms we are interested in are cosine
waves
% find the frequency which fits best from the specified
range
% lower frequency (nm)
fl=2000.0;
% upper frequency (nm)
fu=15000.0;
% step size (nm)
df=10.0;
freq=[fl:df:fu];
% find best fit frequency and starting phase
C=exp(j*2*pi.*t*freq);
d=mean(D.'); % average spectra
vs=C'*(d-mean(d)); % remove mean
[mr,kk]=max(abs(vs)); % find frequency with maximum
amplitude
phase=angle(vs(kk)); % estimate phase
```

-continued

```
% set upper & lower limits for integration
fln=freq(kk)-1/(2*max(t));
fun=freq(kk)+1/(2*max(t));
% matrix S projects onto space of sine waves
S=imag(C*exp(j*phase));
Dp=S'*D;
% obtain linear time varying average
if op1 == 0
    g0=[[1:w1],[w2:w3]];
else
    g0=[1:w1];
end
offset=mean(g0);
g=g0-offset;
% X is the calibration data only
X=Dp(:,g0);
vm=mean(X.').';
[m,n]=size(X);
Y=zeros(size(X));
% project out mean
for k=1:n
    Y(:,k)=X(:,k)*vm.'*vm/(vm.'*X(:,k))-vm;
end
% calculate linear time-varying component
Z=repmat(g,[m,1]).*Y;
vd=mean(Z.').'/mean(g.^2);
M=zeros(size(Dp));
% now project off a time-varying reference for each
data vector
for k=1:size(Dp,2)
    v=vm+op2*(k-offset)*vd;
    M(:,k)=Dp(:,k)*v.'*v/(v.'*Dp(:,k))-v;
end
% reduce range of interest for integration
q=[fix((fln-fl)/df)+1:fix((fun-fl)/df)+1];
s=S'*(S(:,kk).*t);
es=-length(t)*sum(M(q,:))/(2*pi*df*mr*sum(s(q)));
% plot output
figure
plot((es).^1)
xlabel('sample no.')
ylabel('response')
title(plot_title)
% write to file
fid=fopen(outfile,'w');
fprintf(fid,'%6.3f\n',es)
fclose(fid)
```

The invention claimed is:

1. A method of detecting perturbation of a physical system from a reference state associated with a reference parameter ($\omega_0$) to a perturbed state associated with a perturbed parameter ($\omega$), the method including the steps of:
   a) deriving the reference parameter ($\omega_0$);
   b) deriving a reference entity (F) which describes the system's state at the reference parameter ($\omega_0$);
   c) deriving an error entity (E) from the difference between the reference entity (F) and a measurement-related entity (Z) associated with a perturbed state of the system; and
   d) using the error entity (E) to provide an indication of whether or not the system state has been perturbed from the state associated with the reference parameter ($\omega_0$), with the perturbed parameter ($\omega$) having become unequal to the reference parameter ($\omega_0$).

2. A method according to claim 1 wherein the error entity (E) is a vector with multiple members ($E_j$, j=1 to $N_k$) and step d) includes calculating the sum of the error vector's members ($E_j$) to obtain an indication of whether or not the perturbed parameter ($\omega$) has become unequal to the reference parameter ($\omega_0$).

3. A method according to claim 2 wherein the error entity (E) has members characterised by relatively high signal to noise ratio compared other possible members which might otherwise be selected to derive it.

4. A method according to claim 3 wherein the error entity (E) has members derived from a region of a peak in a derivative (F') of the reference entity (F).

5. A method according to claim 1 wherein prior to derivation of the error entity (E) in step c), the measurement-related entity (Z) is normalised by projection on to a space orthogonal to that of the reference entity (F).

6. A method according to claim 1 wherein step d) includes determining the difference ($\omega-\omega_0$) between the perturbed and reference parameters ($\omega, \omega_0$) by error entity normalisation with respect to an entity which is a summation of elements of an entity (F') representing a derivative ($f'(\omega_0, \delta\omega)_e$) of a reference function ($f(\omega_0,\delta\omega)_e$) evaluated at the reference parameter ($\omega_0$), the reference function ($f(\omega_0,\delta\omega)_e$) being represented by the reference entity (F).

7. A method according to claim 1 wherein step b) incorporates;
   a) predicting from the reference parameter ($\omega_0$) a position of a peak in a Fourier transform spectrum of observation data;
   b) selecting a subset of the observation data over the predicted peak and calculating a direct Fourier transform (as herein defined) for the subset; and
   c) analysing the direct Fourier transform in order to derive a more accurate determination of the position of the peak.

8. A method according to claim 1 wherein the reference entity (F) is derived in step b) by a process which includes filtering by projection of an entity on to a set S of pre-determined entities having a range of arguments all of which differ from the reference parameter ($\omega_0$) by less than one tenth of the reference parameter ($\omega_0$).

9. A method according to claim 8 wherein step c) of claim 1 comprising calculating an error entity (E) includes deriving the measurement-related entity (Z) by a process which includes data filtering by projection of a measurement entity (X) on to the set S of pre-determined entities.

10. A method according to claim 1 wherein the reference entity (F) is derived in step b) from an average of a series of observation data vectors (X).

11. A method according to claim 10 wherein the observation data vectors (X) are time-varying and this is taken into account when their average is derived.

12. A method according to claim 11 wherein the reference entity (F) is a sum of a static reference entity and a linearly time-varying entity.

13. A method according to claim 1 wherein the system is a sensor (10) pervaded by a medium having variable composition.

14. A method according to claim 13 wherein the sensor is a porous silicon sensor (10) with pores pervaded by the medium which is a solvent, the perturbed and reference parameters ($\omega, \omega_0$) are optical thicknesses of a region of the sensor (10) pervaded by different solvent compositions and in which interference patterns are generated for derivation of the reference entity (F) and error entity (E).

15. Apparatus for detecting perturbation of a physical system from a reference state associated with a reference parameter ($\omega_0$) to a perturbed state associated with a perturbed parameter ($\omega$), the apparatus including:
   a) a monitoring device for monitoring the physical system to obtain indications of the system's state;
   b) a computer system programmed to process the system state indications to:

i) derive the reference parameter ($\omega_0$);
ii) derive a reference entity (F) which describes the system's state at the reference parameter ($\omega_0$);
iii) derive an error entity (E) from the difference between the reference entity (F) and a measurement-related entity (Z) associated with a perturbed state of the system; and
iv) use the error entity (E) to provide an indication of whether or not the system state has been perturbed from the state associated with the reference parameter ($\omega_0$), with the perturbed parameter ($\omega$) having become unequal to the reference parameter ($\omega_0$).

16. Apparatus according to claim 15 wherein the error entity (E) is a vector with multiple members ($E_j$, j=1 to $N_k$) and the computer system is programmed to calculate the sum of the error vector's members ($E_j$) to obtain an indication of whether or not the perturbed parameter ($\omega$) has become unequal to the reference parameter ($\omega$).

17. Apparatus according to claim 16 wherein the error entity (E) has members characterised by relatively high signal to noise ratio compared other possible members which might otherwise be selected to derive it.

18. Apparatus according to claim 17 wherein the error entity (E) has members derived from a region of a peak in a derivative (F') of the reference entity (F).

19. Apparatus according to claim 15 wherein the computer system is programmed to normalise the measurement-related entity (Z) by projection on to a space orthogonal to that of the reference entity (F) prior to derivation of the error entity (F).

20. Apparatus according to claim 15 wherein the computer system is programmed to determine the difference ($\omega-\omega_0$) between the perturbed and reference parameters ($\omega$, $\omega_0$) by error entity normalisation with respect to an entity which is a summation of elements of an entity (F') representing a derivative ($f'(\omega_0,\delta\omega)_e$) of a reference function ($f(\omega_0,\delta\omega)_e$) evaluated at the reference parameter ($\omega_0$), the reference function ($f(\omega_0,\delta\omega)_e$) being represented by the reference entity (F).

21. Apparatus according to claim 15 characterised in the computer system is programmed to derive the reference entity (F) by;
a) predicting from the reference parameter ($\omega_0$) a position of a peak in a Fourier transform spectrum of observation data;
b) selecting a subset of the observation data over the predicted peak and calculating a direct Fourier transform (as herein defined) for the subset; and
c) analysing the direct Fourier transform in order to derive a more accurate determination of the position of the peak.

22. Apparatus according to claim 15 wherein the computer system is programmed to derive the reference entity (F) by a process which includes filtering by projection of an entity on to a set S of pre-determined entities having a range of arguments all of which differ from the reference parameter ($\omega_0$) by less than one tenth of the reference parameter ($\omega_0$).

23. Apparatus according to claim 22 characterised in the computer system is programmed to calculate the error entity (E) by deriving the measurement-related entity (Z) by a process which includes data filtering by projection of a measurement entity (X) on to the set S of pre-determined entities.

24. Apparatus according to claim 15 wherein the computer system is programmed to derive the reference entity (F) from an average of a series of observation data vectors (X).

25. Apparatus according to claim 24 wherein the observation data vectors (X) are time-varying and the computer system is programmed to take this into account when deriving their average.

26. Apparatus according to claim 25 wherein the reference entity (F) is a sum of a static reference entity and a linearly time-varying entity.

27. Apparatus according to claim 15 wherein the system is a sensor (10) pervaded by a medium having variable composition.

28. Apparatus according to claim 27 wherein the sensor is a porous silicon sensor (10) with pores pervaded by the medium which is a solvent, the perturbed and reference parameters ($\omega$, $\omega_0$) are optical thicknesses of a region of the sensor (10) pervaded by different solvent compositions and in which interference patterns are generated for derivation of the reference entity (F) and error entity (E).

29. A computer program product comprising a computer readable medium containing computer readable instructions for use in detecting perturbation of a physical system from a reference state associated with a reference parameter ($\omega_0$) to a perturbed state associated with a perturbed parameter ($\omega$), the computer readable instructions being for controlling computer apparatus to implement the steps of:
a) deriving the reference parameter ($\omega_0$);
b) deriving a reference entity (F) which describes the system's state at the reference parameter ($\omega_0$);
c) deriving an error entity (E) from the difference between the reference entity (F) and a measurement-related entity (Z) associated with a perturbed state of the system; and
d) using the error entity (E) to provide an indication of whether or not the system state has been perturbed from the state associated with the reference parameter ($\omega_0$), with the perturbed parameter ($\omega$) having become unequal to the reference parameter ($\omega_0$).

30. A computer program product according to claim 29 wherein the error entity (E) is a vector with multiple members ($E_j$, j=1 to $N_k$) and step d) includes calculating the sum of the error vector's members ($E_j$) to obtain an indication of whether or not the perturbed parameter ($\omega$) has become unequal to the reference parameter ($\omega_0$).

31. A computer program product according to claim 30 wherein the error entity (E) has members characterised by relatively high signal to noise ratio compared other possible members which might otherwise be selected for deriving it.

32. A computer program product according to claim 31 wherein the error entity (E) has members derived from a region of a peak in a derivative (F') of the reference entity (F).

33. A computer program product according to claim 29 wherein prior to derivation of the error entity (E) in step c), the measurement-related entity (Z) is normalised by projection on to a space orthogonal to that of the reference entity (F).

34. A computer program product according to claim 29 wherein step d) includes determining the difference ($\omega-\omega_0$) between the perturbed and reference parameters ($\omega$, $\omega_0$) by error entity normalisation with respect to an entity which is a summation of elements of an entity (F') representing a derivative ($f'(\omega_0,\delta\omega)_e$) of a reference function ($f$ ($107_0,\delta\omega)_e$) evaluated at the reference parameter ($\omega_0$), the reference function ($f(\omega_0,\delta\omega)_e$) being represented by the reference entity (F).

35. A computer program product according to claim 29 wherein step b) incorporates:
   a) predicting from the reference parameter ($\omega_0$) a position of a peak in a Fourier transform spectrum of observation data;
   b) selecting a subset of the observation data over the predicted peak and calculating a direct Fourier transform (as herein defined) for the subset; and
   c) analysing the direct Fourier transform in order to derive a more accurate determination of the position of the peak.

36. A computer program product according to claim 29 wherein step b)'s deriving of the reference entity (F) includes filtering by projection of an entity on to a set S of pre-determined entities having a range of arguments all of which differ from the reference parameter ($\omega_0$) by less than one tenth of the reference parameter ($\omega_0$).

37. A computer program product according to claim 36 wherein the step of calculating the error entity (E) includes deriving the measurement-related entity (Z) by a process which includes data filtering by projection of a measurement entity (X) on to the set S of pre-determined entities.

38. A computer program product according to claim 29 wherein the step of deriving the reference entity (F) employs an average of a series of observation data vectors (X).

39. A computer program product according to claim 38 wherein the observation data vectors (X) are time-varying and this is taken into account when their average is derived.

40. A computer program product according to claim 39 wherein the reference entity (F) is a sum of a static reference entity and a linearly time-varying entity.

41. A computer program product according to claim 29 wherein the system is a sensor (10) pervaded by a medium having variable composition.

42. A computer program product according to claim 41 wherein the sensor is a porous silicon sensor (10) with pores pervaded by the medium which is a solvent, the perturbed and reference parameters ($\omega$, $\omega_0$) are optical thicknesses of a region of the sensor (10) pervaded by different solvent compositions and in which interference patterns are generated for derivation of the reference entity (F) and error entity (E).

* * * * *